United States Patent
Walta (10) Patent No.: US 9,421,067 B2
(45) Date of Patent: Aug. 23, 2016

(54) TEST DEVICE (75) Inventor: Johannes Anthonius Walta, Leidschendam (NL)

(73) Assignee: WAMA B.V., Nieuw-Vennep (NL)

( * ) Notice: Subject to any disclaimer, the term of this patent is extended or adjusted under 35 U.S.C. 154(b) by 734 days.

(21) Appl. No.: 13/876,248

(22) PCT Filed: Sep. 28, 2011

(86) PCT No.: PCT/NL2011/050655
§ 371 (c)(1),
(2), (4) Date: May 30, 2013

(87) PCT Pub. No.: WO2012/044165
PCT Pub. Date: Apr. 5, 2012

(65) Prior Publication Data
US 2013/0233236 A1 Sep. 12, 2013

(30) Foreign Application Priority Data

Sep. 28, 2010 (NL) .................................. 2005410

(51) Int. Cl.
*A61B 19/00* (2006.01)
(52) U.S. Cl.
CPC .......... *A61B 19/00* (2013.01); *A61B 2090/702* (2016.02)
(58) Field of Classification Search
CPC ........................ A61B 19/34; A61B 2019/346
See application file for complete search history.

(56) References Cited

U.S. PATENT DOCUMENTS

2006/0263245 A1* 11/2006 Watanabe ................. A61L 2/28
422/400
2007/0008160 A1 1/2007 Nagai et al.

FOREIGN PATENT DOCUMENTS

| DE | 299 09 783 | 12/1999 |
| DE | 201 08 346 | 9/2001 |
| DE | 10 2004 040733 | 3/2006 |
| DE | 10 2004 060289 | 4/2006 |
| EP | 0 709 056 | 5/1996 |
| WO | WO 2008019715 | 2/2008 |

OTHER PUBLICATIONS

NL Search Report and Written Opinion of application PCT/NL2011/050655 dated May 17, 2011, 10 pages.

* cited by examiner

*Primary Examiner* — Paul West
(74) *Attorney, Agent, or Firm* — Thomas | Horstemeyer, LLP (57) ABSTRACT

The invention relates to a test device for confirmation of a cleaning effect of a cleaning device for a hollow medical device, in particular an endoscope, comprising a housing defining at least one test channel to be connected to a cleaning fluid feed line of the cleaning device, wherein said housing defines a location for mounting a plate shaped indicator in the test channel, characterized in that the test device comprises multiple test channels, and in that the indicator comprises a test surface having one or more test samples, wherein the one or more test samples on the test surface of the indicator, when mounted on the mounting location, are arranged in the multiple test channels.

24 Claims, 4 Drawing Sheets

TEST DEVICE

CROSS-REFERENCE TO RELATED APPLICATION

This application is the National Stage of International Application No. PCT/NL2011/050655, filed Sep. 28, 2011, which claims the benefit of NL 2005410, filed Sep. 28, 2010, the contents of which are incorporated by reference as if fully set forth herein.

FIELD OF THE DISCLOSURE

The invention relates to a test device and method to confirm the cleaning effect of a cleaning device for a hollow medical device.

BACKGROUND

It is important that hollow medical devices, in particular endoscopes are properly cleaned between subsequent uses. For this reason special cleaning devices are known which are used to clean hollow medical devices. In such cleaning device the channels within the medical device are connected to feed lines so that each channel can be separately flushed with a cleaning fluid. These cleaning devices are well known, and for instance disclosed in EP 0 709 056.

The cleaning effect of the cleaning device should regularly be tested to make sure that medical devices introduced in the cleaning device are properly cleaned.

It is known to provide a surrogate endoscope which resembles the structure of the real endoscope to test the cleaning effect. By using a surrogate endoscope the expensive endoscope does not have to be used to test the cleaning device.

Plate-shaped indicators may be used to check the cleaning effect of a cleaning device. These indicators comprise a test surface on which a test sample is provided. U.S. 2007/0008160 discloses a sterilization confirmation tester in which plate-shaped indicators are used to test the effect of sterilization.

It may be advantageous to use standard size indicators. However, these indicators do not always fit into the respective channel of the endoscope or the surrogate endoscope. U.S. 2007/0008160 discloses the use of a holder, where the cross section of the holder is widened at the location of the indicator to hold the indicator. At both ends of the holder tubes are connected, which tubes resemble the structure of the endoscope to be cleaned.

Although the tubes are selected to resemble the structure of the endoscope, the widening of the test channel at the location of the indicator, changes the flow characteristics at the location of the indicator. As a result, the cleaning effect of the cleaning device as determined by the indicator may be incorrect when compared to an endoscope channel having a smaller diameter.

This situation may result in cleaning devices being disapproved as they show insufficient cleaning effect on the indicator after testing the cleaning device, while the actual cleaning effect in a real endoscope is sufficient. Also, a cleaning device may be approved for having sufficient cleaning effect, while the actual cleaning of a real endoscope is insufficient.

SUMMARY

An object of the invention is to provide a test device in which the cleaning effect of a cleaning device for hollow medical devices can reliably be tested, or at least to provide an alternative test device for confirmation of a cleaning effect of a cleaning device for a hollow medical device.

According to a first aspect of the invention there is provided a test device for confirmation of a cleaning effect of a cleaning device for a hollow medical device, in particular an endoscope, comprising a housing defining at least one test channel to be connected to a cleaning fluid feed line of the cleaning device, wherein said housing defines a mounting location for mounting a plate shaped indicator in the test channel, characterized in that the test device comprises multiple test channels, and in that the indicator comprises a test surface having one or more test samples, wherein the one or more test samples on the test surface of the indicator, when mounted on the mounting location, are arranged in the multiple test channels.

According to this first aspect of the invention it is proposed to provide an indicator that, when mounted on the test device, is arranged in multiple test channels. In such embodiment only one indicator has to be mounted on the mounting location to provide a test surface in the multiple test channels. This results in efficient use of the test device since one indicator can simultaneously be used for multiple test channels. Furthermore, the test results of multiple channels remain together on the single indicator. This decreases the risk that the test results of different indicators are mixed up.

Preferably, the testing device comprises only one indicator which comprises a single test surface to be arranged in all test channels.

In an alternative embodiment the plate-shaped indicator may comprise two test surfaces at opposite sides of the indicator, wherein each test surface is arranged in one or more test channels. Also, two or more indicators may be provided in the test device, wherein at least one indicator comprises a test surface arranged in at least two test channels.

To test the cleaning effect the test surface may be provided with one or more test samples, wherein the one or more test samples on the test surface of the indicator is/are arranged in the multiple test channels, when the indicator is mounted on the mounting location.

To test the cleaning effect of the cleaning device a test sample is provided on the test surface. The test sample is for instance a known contamination. The test sample is arranged in the test channel so that cleaning fluid from the cleaning device will run along the test sample during testing of the cleaning effect of the cleaning device. After performing a cleaning process, inspection of the test surface will provide an indication of the cleaning effect in the respective test channel. For instance, the cleaning process is only sufficient when the test sample is washed from the part of the test surface arranged in the test channel during the cleaning process.

In an embodiment, the test surface comprises multiple test samples to determine the cleaning effect of the cleaning device, wherein each test sample of the indicator, when mounted on the mounting location, is arranged in only one of the multiple test channels. It is advantageous to provide for each test channel a separate test sample. By inspection of the location of the test samples after the cleaning process, the cleaning effect of the cleaning device may be determined.

In an embodiment, each of the test samples is completely arranged in the respective test channel. This has the advantage that the cleaning effect of the cleaning device can even more reliably be determined. Since the test samples are completely arranged within the test channel, the desired level of cleaning can for example be selected to be that the test samples are completely washed of the test surface. It can easily be determined, for example by visual inspection of the indicator, that the test samples are completely gone or that still some material of the test sample is present on the test surface.

Preferably, the test samples are arranged at some distance from a sharp corner in the test channel, in particular a sharp corner in the test channel formed by the transition of the test surface to another part of the inner surface of the test channel. A sharp corner may have a decreasing effect on the cleaning effect of the cleaning effect in this corner. Therefore, is may be undesirable to have a test sample in such corner. The distance between a corner and the test sample is for example at least 5% of the width of the test channel, preferably at least 10% of the width of the test channel.

In an embodiment, the indicator is a flat plate. A flat plate can reliably be mounted in a mounting location of a test device. However, the plate-shaped indicator may also be provided as a bent plate or a plate of bendable material. Such bent plate or plate of bendable material may for instance be applied in an embodiment of a test device, wherein the test channels are arranged in a circle. The indicator may be made of any suitable material, for instance material used for conventional indicators or endoscope channels, such as plastics material.

In an embodiment, the surface area of the cross section of the test channel at the location of the indicator may be substantially the same as the surface area of the cross section of an actual channel to be cleaned. In an embodiment the shape of the cross section of the test channel at the location of the indicator may also be the same as the shape of the cross section of the actual channel to be cleaned. As a result, the cleaning effect in the test device is substantially the same as the cleaning effect in the actual channel to be cleaned, and, as a result, the cleaning effect can more reliably be determined.

In an embodiment, the test surface of the indicator defines a part of the inner surface of the test channel. The indicator does not have to be completely arranged in the channel, and the location for mounting the indicator can relative easily be provided at the outer side of the housing when an opening is provided between the test channel and the outer surface of the housing.

As an alternative, the indicator may be partially arranged in the test channel so that cleaning fluid can flow at the side of the test surface and the opposite side of the indicator. Edges of the indicator including a part of the test surface may be held by the structure defining the channels, so that this part of the test surface is not located in the test channel, and cannot be used for testing.

In an embodiment, the test device comprises a surrogate endoscope structure designed to simulate one or more endoscope types, wherein the cleaning effect of the cleaning device is determined by cleaning said surrogate endoscope structure. As an alternative the test device may be a separate device which can be mounted to an endoscope or surrogate endoscope to confirm the cleaning effect of a cleaning device for endoscopes.

According to a second aspect of the invention a test device is provided for confirmation of a cleaning effect of a cleaning device for a hollow medical device, in particular an endoscope, comprising a housing defining at least one test channel to be connected to a cleaning fluid feed line of the cleaning device, wherein said housing defines a location for mounting a plate shaped indicator in the test channel, characterized in that the at least one test channel comprises at the location of the indicator substantially the same structure as a corresponding channel of the hollow medical device, and in that the test surface is only partly arranged in the test channel.

By providing substantially the same structure at the location of the indicator as a channel of a endoscope to be cleaned in the cleaning device, the same flow characteristics can be obtained at the location of the indicator resulting in more reliable determination of the cleaning effect of the cleaning effect.

It is remarked that the test device of the invention is designed for at least one specific hollow medical device. Thus, during the design of the test device the design of the hollow medical device to be cleaned is known, and the structure of the channel of the test device can thus be adapted to the specific structure of the corresponding channel of the hollow medical device to be cleaned. A test device may comprise multiple test channels, wherein different predefined selections of test channels substantially correspond to different hollow medical devices. Such test device can be used for different hollow medical devices.

The same structure between the test channel and the corresponding channel of the endoscope may for instance be obtained by matching the surface area of the cross section of the test channel at the location of the indicator to the surface area of the cross section of the actual channel to be cleaned. In an embodiment the shape of the cross section of the test channel at the location of the indicator may also be the same as the shape of the cross section of the actual channel to be cleaned.

However, the provision of the same structure at the location of the indicator may result in that the plate-shape indicator cannot be arranged in the test channel since the dimensions of the indicator are too large. Therefore, the test surface of the indicator, i.e. the side of the indicator on which a test sample is provided, is only partly arranged in the test channel. This may have the effect that only a part of the test sample arranged on the test surface is placed within the channel during confirmation of the cleaning effect of the cleaning device. After the cleaning process only the part of the test sample arranged in the test channel should be checked for the cleaning effect of the cleaning device.

In an embodiment, the test surface of the indicator defines a part of the inner surface of the channel. The indicator does not have to be completely arranged in the channel, and the location for mounting the indicator can relative easily be provided at the outer side of the housing when an opening is provided between the test channel and the outer surface of the housing.

As an alternative, the indicator may be partially arranged in the test channel so that cleaning fluid can flow at the side of the test surface and the opposite side of the indicator. Edges of the indicator including a part of the test surface may be held by the structure defining the channels, so that this part of the test surface is not located in the test channel, and cannot be used for testing.

In an embodiment, the test device comprises multiple test channels to be connected to a cleaning fluid feed line of the cleaning device, wherein the housing comprises for each of said multiple test channels a location for mounting a plate-shaped indicator, wherein, after mounting, a test surface of said indicator is arranged at least partially in the test channel of the test device. In such embodiment surface areas of cross sections of the test channels at the location of the indicator may substantially correspond to surface areas of cross sections of the respective channels of a hollow medical device to be cleaned.

In practice, an endoscope may have multiple channels which are cleaned simultaneously in a cleaning device. By providing a test device with multiple test channels the cleaning effect of the cleaning device can be tested simultaneously for these multiple channels.

In an embodiment, the test device comprises a surrogate endoscope structure designed to simulate one or more endoscope types, wherein the cleaning effect of the cleaning device is determined by cleaning said surrogate endoscope structure. As an alternative the test device may be a separate device which can be mounted to an endoscope or surrogate endoscope to confirm the cleaning effect of a cleaning device for endoscopes.

The invention also relates to a method for confirmation of a cleaning effect of a cleaning device for a hollow medical device, in particular an endoscope, using a test device described herein, including any one or more embodiments of the test device described herein, comprising the steps of: mounting a plate shaped indicator on the location for mounting; cleaning a hollow medical device or a surrogate device with the cleaning device; dismounting the indicator; and determine the cleaning effect obtained in the cleaning step on the basis of the part of the test surface arranged in the test channel or test channels during the cleaning step.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
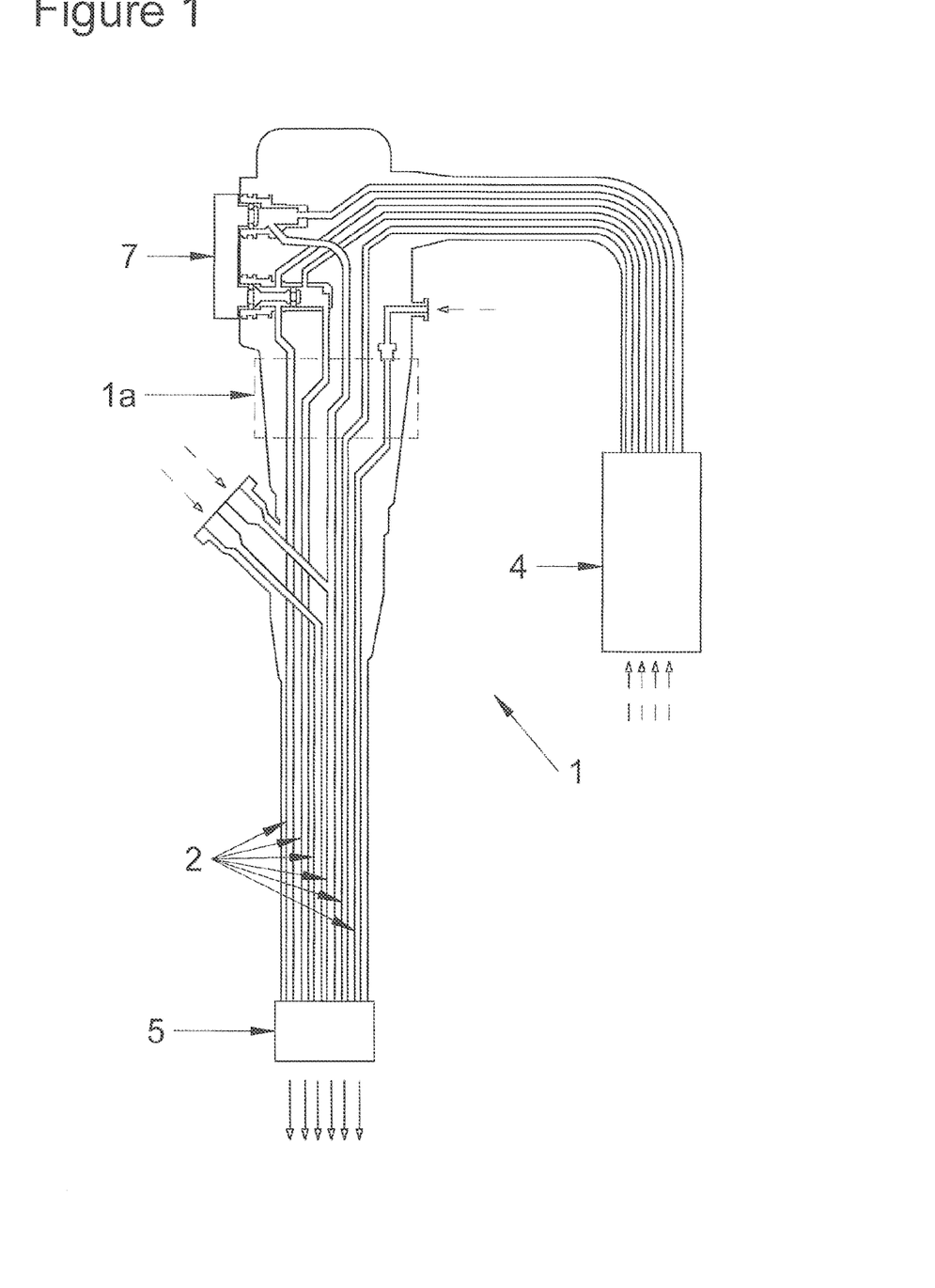
FIG. 1 depicts a surrogate endoscope comprising a test device according to an embodiment of the invention.

FIG. 1 depicts a surrogate endoscope 1 to be used in a cleaning device to clean endoscopes to confirm the cleaning effect of the cleaning device. In such cleaning device channels of an endoscope to be cleaned are connected to feed lines with cleaning fluid.

To check the cleaning effect of the cleaning device the surrogate endoscope 1 having test channels 2 with a similar structure as a real endoscope may be arranged in the cleaning device. The advantage of the use of such surrogate endoscope 1 is that a real endoscope does not have to be used for test purposes.

The surrogate endoscope 1 shown in FIG. 1 comprises more test channels 2 than a number of known endoscope types. By selection of different test channels two different types of endoscopes can be simulated. Thus, the surrogate endoscope 1 can be simultaneously be used to test the cleaning effect of the cleaning device for different types of endoscopes.

When the surrogate endoscope 1 is arranged in a cleaning device, the test channels 2 of the surrogate endoscope 2 may be connected to feed lines of the cleaning device to introduce cleaning fluid into the test channels 2. These feed lines for entrance of the cleaning fluid in the test channels 2 are indicated by dashed arrows. Since the structure of the surrogate endoscope 1 substantially corresponds to one or more types of endoscopes, the cleaning effect obtained in the surrogate endoscope is representative for the cleaning effect obtained in one of the one or more types of endoscopes.

The surrogate endoscope 1 comprises a first test device 4 and a second test device 5 arranged at the entrance and the exit of cleaning fluid in the surrogate endoscope 1, respectively. A similar test device could be arranged in the control body of the surrogate endoscope, for instance in the area indicated by a box 1a. The first and second test device 4, 5 are designed to hold a number of plate shaped indicators 6 (See FIGS. 2-7), which are provided to determine the cleaning effect obtained by the cleaning device in the test channels 2 of the surrogate endoscope 1. A separator 7 is provided to create separate test channels 2 in the surrogate endoscope 1. Such separator 7 is also used during cleaning a real endoscope in the cleaning device. It is remarked that in alternative embodiments of cleaning devices the cleaning fluid may be introduced at the valve housing. In such case a cleaning fluid connector is provided instead of a separator 7.

The test channels 2 may, corresponding to the respective channels of the one or more endoscope types to be cleaned by the cleaning device, have varying cross sections, for instance in the range of 1 mm$^2$-100 mm$^2$. In case the channels have a circular cross section, the diameter of the channels may for instance be in the range of 1 mm to 5 mm.

To check the cleaning effect, the plate-shaped indicators 6 have a test surface which is partially arranged in the test channel 2. The test surface is a side of the indicator 6 which is provided with a test sample having a known contamination. By inspection or further testing of the test sample after cleaning of the surrogate endoscope 1 the cleaning effect of the cleaning device can be determined.

Figure 2:
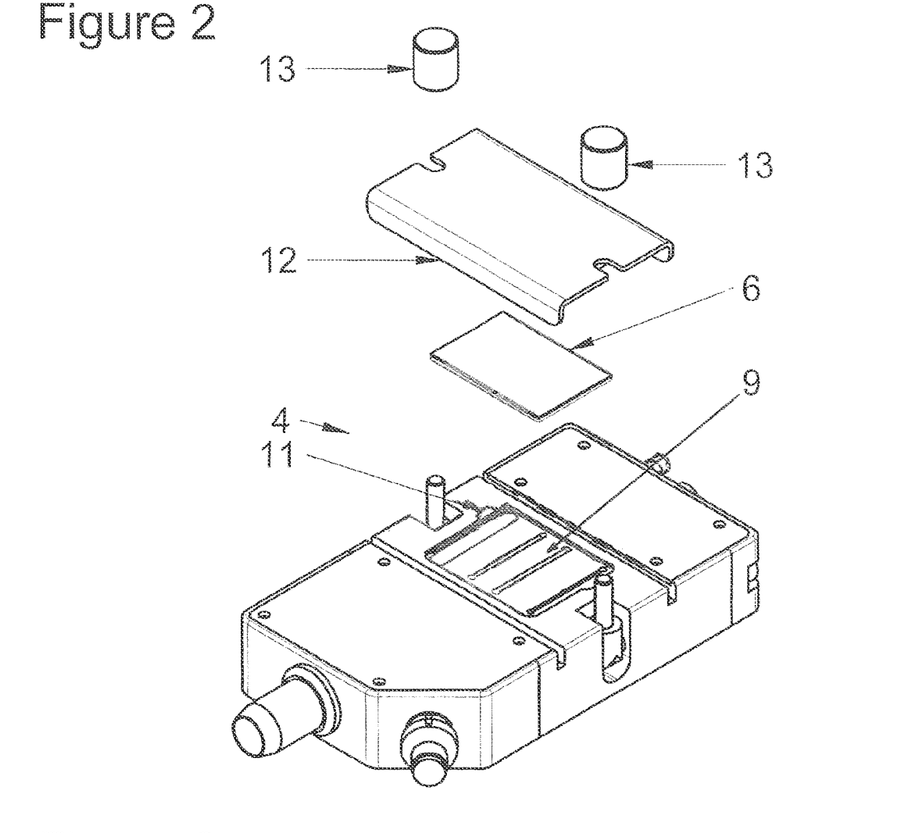
FIG. 2 depicts a test device according to an embodiment of the invention.
Figure 3:
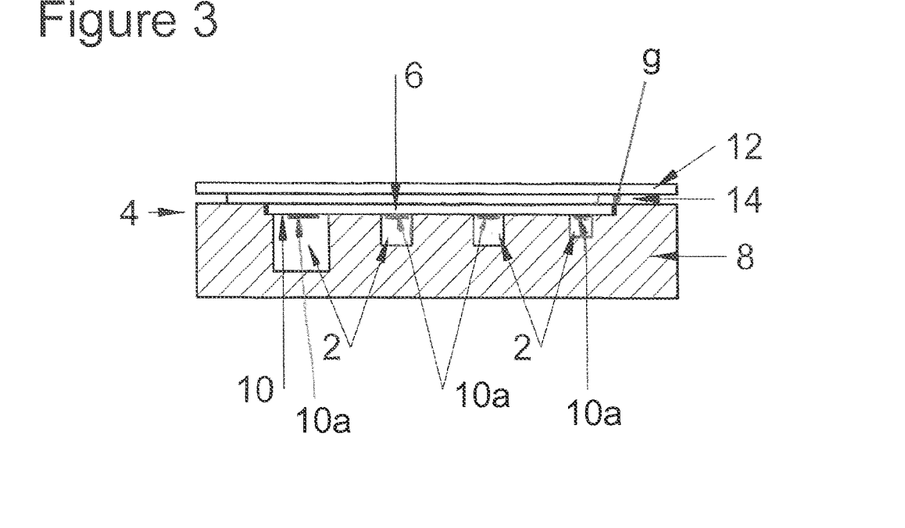
FIG. 3 depict s a cross section of the embodiment of FIG. 2.

FIG. 2 shows a first embodiment of a test device 4 comprising a single indicator 6 for all test channels 2. FIG. 3 shows a cross section of the first test device 4.

The first test device 4 comprises four test channels 2 arranged in a housing 8 resembling four channels of an endoscope. It is clear that not all the test channels 2 have the same cross section. The surface area of the cross section of these test channels is chosen substantially the same as the surface area of the cross section of corresponding channels of the endoscope(s) to be cleaned with the cleaning device. The shape of the cross section of the test channels 2, for instance circular or rectangular, may be the same as or different as the shape of the cross section of the channel of an endoscope to be cleaned.

The housing 8 comprises a recess forming a single location 9 for mounting a plate shaped indicator 6 in the test device 4. Between the location 9 and the test channels 2 an opening is provided so that a part of a test surface 10 of the indicator 6 is arranged in the location 9 and forms an inner surface of the test channel 2. In this way the test surface 10 of the indicator 6 is arranged in the test channel 2 even though the dimensions of test channels 2 do not allow the indicator 6 to be completely arranged in one of the test channels 2.

The indicator 6 is a plate shaped element, comprising a test surface 10. The test surface 10 is provided with a number of test samples 10*a*. Each of the test samples 10*a* is aligned with one of the test channels 2 so that each test sample 10*a* is completely arranged in one of the test channels 2.

The advantage of arranging the test sample completely in the test channel 2 is that washing of the contamination of the test sample can reliably be determined by inspection of the indicator 6 after cleaning the test channels 2 with the cleaning device.

Further, the test samples 10*a* are spaced from the sharp corners where the test surface 10 meet the inner surface of the test channels 2 defined by the housing 8. The distance between the corner and the test sample may for instance be at least 5% of the width of the test channel 2, preferably at least 10% of the width of the test channel 2.

The indicator 6 may have a rectangular shape with dimensions of 20 mm to 50 mm by 20 to 50 mm. The indicator may be made of any suitable material, for example the same material as conventional indicators or material of endoscope channels, such as plastics material.

The circumference of the recess forming the mounting location 9 substantially corresponds with the shape of the indicator 6 so that the indicator 6 easily and reliably can be positioned in the location 9, whereby the test samples 10 a are reliably aligned with the respective test channels 2. Further recesses 11 slightly larger than finger tops are provided for easily picking up and placing the indicator 6 in the location 9.

A lid 12 is provided to sealingly engage the indicator 6 in the location 9. The lid 12 can be locked in this sealing position by lid holders 13 or any other suitable means. The lid 12 comprises a rubber pad 14 to hold the indicator 6 in sealing engagement with the housing 8 so that, during use, no cleaning fluid can leave the test channels between the indicator 6 and the housing 8.

Figure 4:
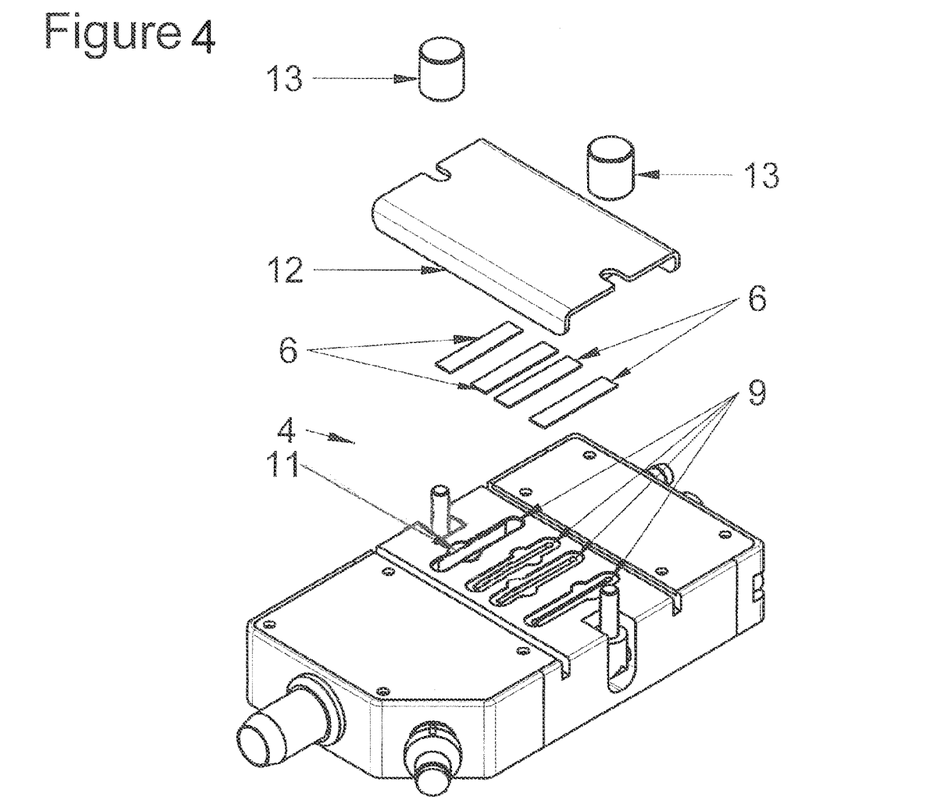
FIG. 4 depicts a test device according to a second embodiment of the invention.

FIG. 4 shows a second embodiment of the first test device 4 wherein standard indicators 6 may be used without the need to increase the cross section of the test channel at the location of the indicators 6.

The indicators 6, for instance available from Simicon, Germany or Healthmark Industries Company, U.S.A, typically have a length of 20 mm to 50 mm and a width of 4 mm to 10 mm. These indicators will not fit in all test channels. However, it advantageous to use these standard indicators. Increasing the cross section is however also undesirable as it would influence the flow characteristics in the test channel 2, and may therefore result in unreliable testing of the cleaning effect of the cleaning device.

Figure 5:
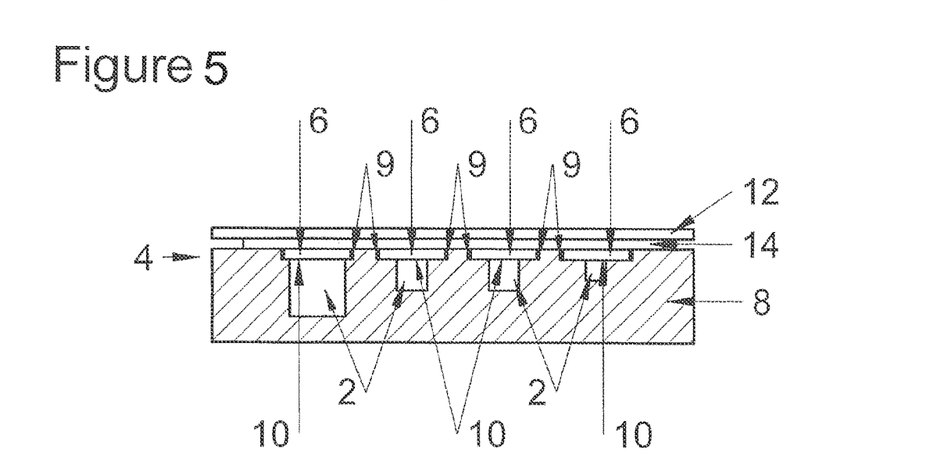
FIG. 5 depicts a cross section of the embodiment of FIG. 4.

The test device 4 comprises four test channels 2 arranged in a housing 8 resembling four channels of an endoscope. FIG. 5 shows a cross section of the test device 4 with the test channels 2. It is clear that not all the test channels 2 have the same cross section. The surface area of the cross section of these test channels is chosen substantially the same as the surface area of the cross section of corresponding channels of the real endoscope(s). The shape of the cross section of the test channels 2, for instance circular or rectangular, may be the same as or different as the shape of the cross section of the channel of an endoscope to be cleaned.

The housing 8 further comprises four locations 9 for mounting the plate shaped indicators 6. Between each of the locations 9 and the test channels 2 an opening is provided so that a part of a test surface 10 of the indicator 6 is arranged in the location 9 and forms an inner surface of the test channel 2. In this way the test surface of the indicator is arranged in the test channel 2 even though the dimensions of test channel 2 do not allow the indicator 6 to be completely arranged in the test channel 2. The locations 9 are formed by recesses in the housing 8. The circumference of the recesses forming the locations 9 substantially corresponds with the shape of the indicators 6 so that the indicators easily and reliably can be placed in the locations 9. Further recesses 11 slightly larger than finger tops are provided for easily picking up and placing the indicators 6 in the locations 9.

A lid 12 is provided to sealingly engage the indicators 6 in the locations 9. The lid 12 can be locked in this sealing position by lid holders 13 or any other suitable means. The lid 12 comprises a rubber pad 14 to hold the indicators 6 in sealing engagement with the housing 8 so that, during use, no cleaning fluid can leave the test channels between the indicators 6 and the housing 8.

Figure 6:
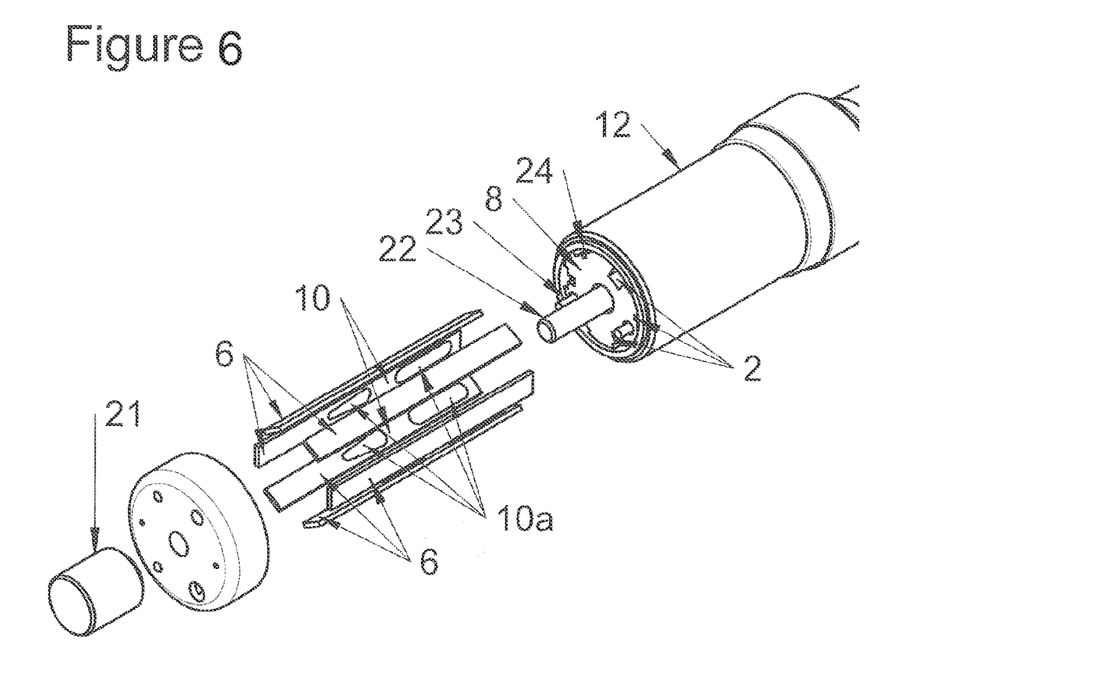
FIG. 6 depicts a test device according to a third embodiment of the invention.

FIG. 6 shows the second test device 5 in more detail. The housing 8 has a cylindrical shape and comprises six test channels 2. For each of the test channels 2, the housing defines a location 9 for mounting an indicator 6. The locations 9 are formed by recesses in the housing 8. A cover 12 surrounds the housing 8 to hold the indicators 6 in the housing 8.

Figure 7:
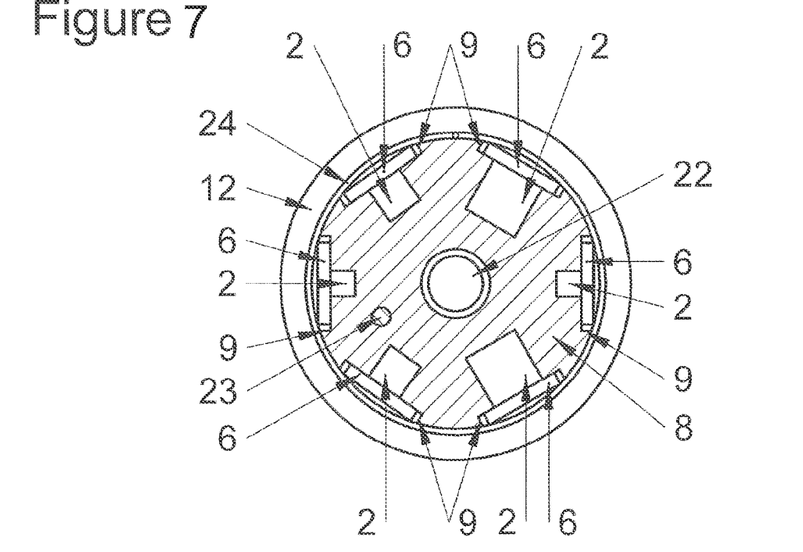
FIG. 7 depicts a cross section of the embodiment of FIG. 6.

FIG. 7 shows a cross section of the housing 8 and the cover 12, while indicators 6 are arranged in the locations 9. The cross sections of the test channels 2 differ with respect to each other, but substantially correspond to the cross sections of the channels of a medical device to be cleaned by the cleaning device. As a result, the cleaning action of the cleaning device can reliably be tested by the testing device 5.

The indicators 6 can be placed in a longitudinal direction at the locations 9. The indicators 6 should be placed such that the test surfaces 10 form an inner surface of the test channels 2 so that the test samples 10*a* are at least partially arranged in the test channels 2. After placement of the indicators 6, a cap 20 can be arranged on the housing to keep the indicators 6 in the locations 9. The cap 20 comprises six openings having cross sections matching with the cross sections of the test channels 2. A cap holder 21 is provided to lock the cap on the housing. The cap holder 21 may be screwed or snapped on a locking pin 22 with screw thread or a snap rim, extending from the housing 8.

The test device 5 further comprises a positioning pin 23 extending from the housing 8. The positioning pin 23 can be placed in an associated positioning hole (not shown) in the cap 20. This positioning pin 23 and position hole are used to mount the cap 20 in a correct rotational position with respect to the housing so that the openings in the cap 20 are aligned with the respective test channels 2.

One or more ring-shaped springs 24 may be provided to sealingly engage the indicators in the locations 9 so that no cleaning fluid will leak between the channel 2 and the indicator 6. Any other device or solution to avoid leakage may also be used.

It is remarked that in an alternative embodiment of the second test device 5, the indicators 6 may be replaced by a a single indicator 6 formed of a bent plate or a plate of bendable material having a test surface 10 comprising at least one test sample 10*a* for each test channel 2. Preferably, each test samply is completely arranged within a test channel 2. In such embodiment only one indicator 6 is required for all test channels 2. In alternative embodiment two or more indicators 6 may be provided wherein at least one of indicators 6 forms a part of the inner surface of at least two test channels 2.

Hereinabove the test devices 4,5 are described as an integral part of a larger test device, i.e. the surrogate endoscope 1. However, the test devices 4,5, may also be provided as separate parts which can be connected to a surrogate endoscope or a real endoscope to validate the cleaning effect of the cleaning device.

Hereinabove, the term cleaning or to clean is used to describe an action of reprocessing a hollow medical device, in particular endoscope for subsequest use. This action may comprise disinfection or sterilization of the medical device. Correspondingly, the term cleaning fluid may relate to a cleaning agent, disinfection agent, or fluid for sterilization of the medical device.

The invention claimed is:

1. A test device for confirmation of a cleaning effect of a cleaning device for a hollow medical device, comprising a housing defining at least one test channel to be connected to a cleaning fluid feed line of the cleaning device,
wherein said housing defines a mounting location for mounting a plate shaped indicator in the test channel, wherein the test device comprises multiple test channels, and in that the indicator comprises a test surface having one or more test samples, wherein the one or more test samples on the test surface of the indicator, when mounted on the mounting location, are arranged in the multiple test channels.

2. The test device of claim 1, wherein the test surface comprises multiple test samples used to determine the cleaning effect of the cleaning device, wherein each test sample of the indicator, when mounted on the mounting location, is arranged in one of the multiple test channels.

3. The test device of claim 2, wherein each of the test samples is completely arranged in the respective test channel.

4. The test device claim 1, wherein the indicator is a flat plate.

5. A test device for confirmation of a cleaning effect of a cleaning device for a hollow medical device, comprising a housing defining at least one test channel to be connected to a cleaning fluid feed line of the cleaning device,
wherein said housing defines a location for mounting a plate shaped indicator in the test channel,
wherein the at least one test channel comprises at the location of the indicator the same structure as a corresponding channel of the hollow medical device to be cleaned, and in that a test surface of the indicator is only partly arranged in the test channel.

6. The test device of claim 5, wherein the test surface of the indicator defines a part of the inner surface of the test channel.

7. The test device of claim 5, wherein a surface area of a cross section of the test channel at the location of the indicator substantially corresponds to a surface area of a cross section of the channel of a hollow medical device to be cleaned.

8. The test device of claim 5, wherein the test device comprises multiple test channels to be connected to a cleaning fluid feed line of the cleaning device, wherein the housing comprises for each of said multiple test channels a location for mounting a plate-shaped indicator, wherein, after mounting, a test surface of said indicator is arranged at least partially in the test channel of the test device.

9. The test device of claim 5, wherein the housing comprises a recess substantially corresponding to a circumference of the indicator, wherein an opening is provided between said recess and the test channel.

10. The test device of claim 9, wherein the test device comprises a lid to be placed on an indicator arranged in the recess to sealingly engage the indicator in the recess.

11. The test device of claim 9, wherein the housing comprises multiple recesses, each recess being configured to receive an indicator.

12. The test device of claim 5, wherein the test device comprises a surrogate endoscope structure designed to simulate one or more endoscope types, wherein the cleaning effect of the cleaning device is determined by cleaning said surrogate endoscope structure.

13. The test device of claim 12, wherein the location for mounting the indicator is arranged at the beginning and/or at the end of a test channel in the surrogate endoscope.

14. The test device of claim 5, wherein the test device comprises a cylindrical housing and a cover, the circumference of the housing defining one or more locations for mounting one or more indicators, the cover being provided to hold the one or more indicators in the one or more locations.

15. A test device for confirmation of a cleaning effect of a cleaning device for a hollow medical device, comprising a housing defining at least one test channel to be connected to a cleaning fluid feed line of the cleaning device,
wherein said housing defines a location for mounting a plate shaped indicator in the test channel, the housing comprising a recess to receive the plate shaped indicator, wherein an opening is provided between said recess and the test channel, wherein the test device comprises multiple test channels to be connected to a cleaning fluid feed line of the cleaning device, wherein the housing comprises for each of said multiple test channels a location for mounting a plate-shaped indicator, wherein, after mounting, a test surface of said indicator is arranged at least partially in the test channel of the test device.

16. The test device of claim 15, wherein the test surface of the indicator defines a part of the inner surface of the test channel.

17. The test device of claim 15, wherein a surface area of a cross section of the test channel at the location of the indicator substantially corresponds to a surface area of a cross section of the channel of a hollow medical device to be cleaned.

18. The test device of claim 15, wherein the test device comprises a lid to be placed on an indicator arranged in the recess to sealingly engage the indicator in the recess.

19. The test device of claim 15, wherein the housing comprises multiple recesses, each recess being configured to receive an indicator.

20. The test device of claim 15, wherein the test device comprises a surrogate endoscope structure designed to simulate one or more endoscope types, wherein the cleaning effect of the cleaning device is determined by cleaning said surrogate endoscope structure.

21. The test device of claim 15, wherein the location for mounting the indicator is arranged at the beginning and/or at the end of a test channel in the surrogate endoscope.

22. The test device of claim 15, wherein the test device comprises a cylindrical housing and a cover, the circumference of the housing defining one or more locations for mounting one or more indicators, the cover being provided to hold the one or more indicators in the one or more locations.

23. A method for confirmation of a cleaning effect of a cleaning device for a hollow medical device, using a test device according to claim 15, comprising the steps of:

mounting a plate shaped indicator on the location for mounting;

cleaning a hollow medical device or a surrogate device with a cleaning device;

dismounting the indicator; and determining the cleaning effect obtained in the cleaning step on the basis of a part of the test surface arranged in the test channel or test channels during the cleaning step.

24. A test device for confirmation of a cleaning effect of a cleaning device for a hollow medical device, comprising a housing defining at least one test channel to be connected to a cleaning fluid feed line of the cleaning device, wherein said housing defines a location for mounting a plate shaped indicator in the test channel, the housing comprising a recess to receive the plate shaped indicator, wherein an opening is provided between said recess and the test channel, and wherein the housing comprises a recess substantially corresponding to a circumference of the indicator, wherein an opening is provided between said recess and the test channel.

* * * * *